US009962837B2

(12) United States Patent
Chen et al.

(10) Patent No.: US 9,962,837 B2
(45) Date of Patent: May 8, 2018

(54) SYSTEM AND METHOD OF CONTROLLING ROBOT BY BRAIN ELECTRICAL SIGNALS

(71) Applicants: HONG FU JIN PRECISION INDUSTRY (WuHan) CO., LTD., Wuhan (CN); HON HAI PRECISION INDUSTRY CO., LTD., New Taipei (TW)

(72) Inventors: Tsung-Han Chen, New Taipei (TW); Shou-Han Chung, New Taipei (TW); Chin-Teng Lin, New Taipei (TW); Li-Wei Ko, New Taipei (TW); Shi-An Chen, New Taipei (TW)

(73) Assignees: HONG FU JIN PRECISION INDUSTRY (WuHan) CO., I, Wuhan (CN); HON HAI PRECISION INDUSTRY CO., LTD., New Taipei (TW)

(*) Notice: Subject to any disclaimer, the term of this patent is extended or adjusted under 35 U.S.C. 154(b) by 80 days.

(21) Appl. No.: 15/076,677

(22) Filed: Mar. 22, 2016

(65) Prior Publication Data
US 2017/0210010 A1    Jul. 27, 2017

(30) Foreign Application Priority Data
Jan. 22, 2016    (TW) .............................. 105101985 A

(51) Int. Cl.
*B25J 9/00* (2006.01)
*B25J 9/16* (2006.01)
(Continued)

(52) U.S. Cl.
CPC .............. *B25J 9/1694* (2013.01); *A61B 5/048* (2013.01); *A61B 5/04012* (2013.01); *A61B 5/7435* (2013.01); *A61F 4/00* (2013.01); *B25J 11/009* (2013.01); *G06F 3/015* (2013.01); *A61B 2503/20* (2013.01); *G05B 2219/45111* (2013.01)

(58) Field of Classification Search
CPC combination set(s) only.
See application file for complete search history.

(56) References Cited

U.S. PATENT DOCUMENTS 5,063,492 A * 11/1991 Yoda ........................ B25J 9/161
700/61
5,153,923 A * 10/1992 Matsuba ................... G06N 3/04
358/1.1
(Continued)

FOREIGN PATENT DOCUMENTS

CA             2642401 A1 *  5/2010 ............... G06N 3/02

*Primary Examiner* — Jonathan L Sample
(74) *Attorney, Agent, or Firm* — ScienBiziP, P.C.

(57) ABSTRACT

A system for controlling a robot by brain electrical signal, includes a screen, an electronic signal detection device, and a host computer. The screen shows a plurality of icons thereon, and the plurality of icons flashes at different frequencies. The electrical signal detection device detects brain electrical signal when one of the plurality of icons is stared. The host computer stores a plurality of personal reference parameters corresponding to the plurality of icons of the screen. The host computer processes the brain electrical signal to get parameters of use, and compares the parameters of use with the plurality of personal reference parameters to choose and execute the icon which is stared.

18 Claims, 12 Drawing Sheets

(51) Int. Cl.
*B25J 11/00* (2006.01)
*A61B 5/00* (2006.01)
*A61F 4/00* (2006.01)
*A61B 5/04* (2006.01)
*A61B 5/048* (2006.01)
*G06F 3/01* (2006.01)

(56) References Cited

U.S. PATENT DOCUMENTS

| | | | | |
|---|---|---|---|---|
| 5,363,858 A * | 11/1994 | Farwell | | A61B 5/0478 600/383 |
| 5,648,709 A * | 7/1997 | Maeda | | G05B 17/02 318/568.1 |
| 5,649,061 A * | 7/1997 | Smyth | | A61B 3/113 250/221 |
| 7,058,445 B2 * | 6/2006 | Kemere | | A61B 5/0476 600/544 |
| 7,482,775 B2 * | 1/2009 | Zaier | | B62D 57/032 318/568.12 |
| 7,546,158 B2 * | 6/2009 | Allison | | G06F 3/015 60/545 |
| 7,813,544 B2 * | 10/2010 | Fukaya | | G06K 9/00248 382/118 |
| 7,826,894 B2 * | 11/2010 | Musallam | | A61F 2/68 600/378 |
| 8,175,686 B2 * | 5/2012 | Utsugi | | G06F 3/011 600/310 |
| 8,433,663 B2 * | 4/2013 | Rickert | | G06K 9/00536 623/24 |
| 8,812,096 B2 * | 8/2014 | Flaherty | | A61F 2/50 600/544 |
| 8,864,846 B2 * | 10/2014 | Herr | | A61F 2/66 623/25 |
| 8,868,174 B2 * | 10/2014 | Sato | | A61B 5/0476 600/473 |
| 9,050,200 B2 * | 6/2015 | Digiovanna | | A61F 2/68 |
| 9,118,775 B2 * | 8/2015 | Lim | | G06F 3/015 |
| 9,373,088 B2 * | 6/2016 | Nuyujukian | | G06N 99/005 |
| 9,477,317 B1 * | 10/2016 | Clements | | G06F 3/017 |
| 9,717,440 B2 * | 8/2017 | Abdelghani | | A61B 5/04888 |
| 9,730,816 B2 * | 8/2017 | Leuthardt | | A61F 2/72 |
| 2002/0198604 A1 * | 12/2002 | Schulman | | A61B 5/0031 623/25 |
| 2003/0023319 A1 * | 1/2003 | Andersen | | A61F 2/68 623/24 |
| 2004/0073414 A1 * | 4/2004 | Bienenstock | | G06F 3/015 703/2 |
| 2005/0017870 A1 * | 1/2005 | Allison | | G06F 3/015 340/4.13 |
| 2005/0119791 A1 * | 6/2005 | Nagashima | | B25J 9/161 700/253 |
| 2005/0159668 A1 * | 7/2005 | Kemere | | A61B 5/0476 600/544 |
| 2005/0228515 A1 * | 10/2005 | Musallam | | A61F 2/68 700/83 |
| 2005/0267597 A1 * | 12/2005 | Flaherty | | A61B 5/0031 623/24 |
| 2006/0049957 A1 * | 3/2006 | Surgenor | | A61B 5/0031 340/4.1 |
| 2006/0084858 A1 * | 4/2006 | Marks | | A61B 5/16 600/407 |
| 2006/0167530 A1 * | 7/2006 | Flaherty | | A61B 5/04001 607/62 |
| 2006/0173259 A1 * | 8/2006 | Flaherty | | A61B 5/0031 600/331 |
| 2006/0189900 A1 * | 8/2006 | Flaherty | | A61F 2/50 600/595 |
| 2006/0241356 A1 * | 10/2006 | Flaherty | | A61B 5/04 600/301 |
| 2006/0241788 A1 * | 10/2006 | Srinivasan | | B25J 9/1694 700/56 |
| 2008/0055133 A1 * | 3/2008 | Chakrabartty | | H03M 3/466 341/143 |
| 2008/0070752 A1 * | 3/2008 | Einav | | A61B 5/103 482/7 |
| 2008/0112885 A1 * | 5/2008 | Okunev | | A61B 1/00016 424/9.1 |
| 2008/0177196 A1 * | 7/2008 | Burdick | | A61B 5/04001 600/544 |
| 2010/0137734 A1 * | 6/2010 | Digiovanna | | A61F 2/68 600/545 |
| 2011/0218453 A1 * | 9/2011 | Hirata | | A61B 5/7267 600/544 |
| 2011/0224572 A1 * | 9/2011 | Gilja | | A61F 2/72 600/545 |
| 2011/0238685 A1 * | 9/2011 | Garcia Molina | | A61B 5/0476 707/769 |
| 2011/0307079 A1 * | 12/2011 | Oweiss | | A61B 5/048 623/27 |
| 2012/0059273 A1 * | 3/2012 | Meggiolaro | | A61B 5/048 600/544 |
| 2012/0075168 A1 * | 3/2012 | Osterhout | | G02B 27/017 345/8 |
| 2012/0078381 A1 * | 3/2012 | Vinjamuri | | A61B 5/04001 623/25 |
| 2012/0095619 A1 * | 4/2012 | Pack | | G05D 1/0038 701/2 |
| 2012/0194551 A1 * | 8/2012 | Osterhout | | G02B 27/0093 345/633 |
| 2012/0194553 A1 * | 8/2012 | Osterhout | | G02B 27/0093 345/633 |
| 2013/0165812 A1 * | 6/2013 | Aksenova | | A61F 2/72 600/544 |
| 2014/0058483 A1 * | 2/2014 | Zao | | A61N 5/06 607/88 |
| 2014/0210745 A1 * | 7/2014 | Chizeck | | G06F 3/015 345/173 |
| 2014/0277582 A1 * | 9/2014 | Leuthardt | | A61F 2/54 623/25 |
| 2014/0282746 A1 * | 9/2014 | Lin | | H04N 21/482 725/61 |
| 2014/0330404 A1 * | 11/2014 | Abdelghani | | A61B 5/0476 700/83 |
| 2015/0245928 A1 * | 9/2015 | Kao | | G06F 3/015 700/90 |

* cited by examiner

SYSTEM AND METHOD OF CONTROLLING ROBOT BY BRAIN ELECTRICAL SIGNALS

CROSS-REFERENCE TO RELATED APPLICATIONS

This application claims priority to Taiwanese Patent Application No. 105101985, filed on Jan. 22, 2016, the contents of which are incorporated by reference herein.

FIELD

The subject matter herein relates to a system and a method of controlling robot by brain electrical signals.

BACKGROUND

A brain-machine interface is a direct communication and control path established between human brain and computer or other electronic devices. Through this path, one can express himself or operate apparatus directly by his brain activity of brain without speech of motion. Therefore, it is useful for paralysed patients or old folks.

BRIEF DESCRIPTION OF THE DRAWINGS

Implementations of the present technology will now be described, by way of example only, with reference to the attached figures.

DETAILED DESCRIPTION

Figure 1:
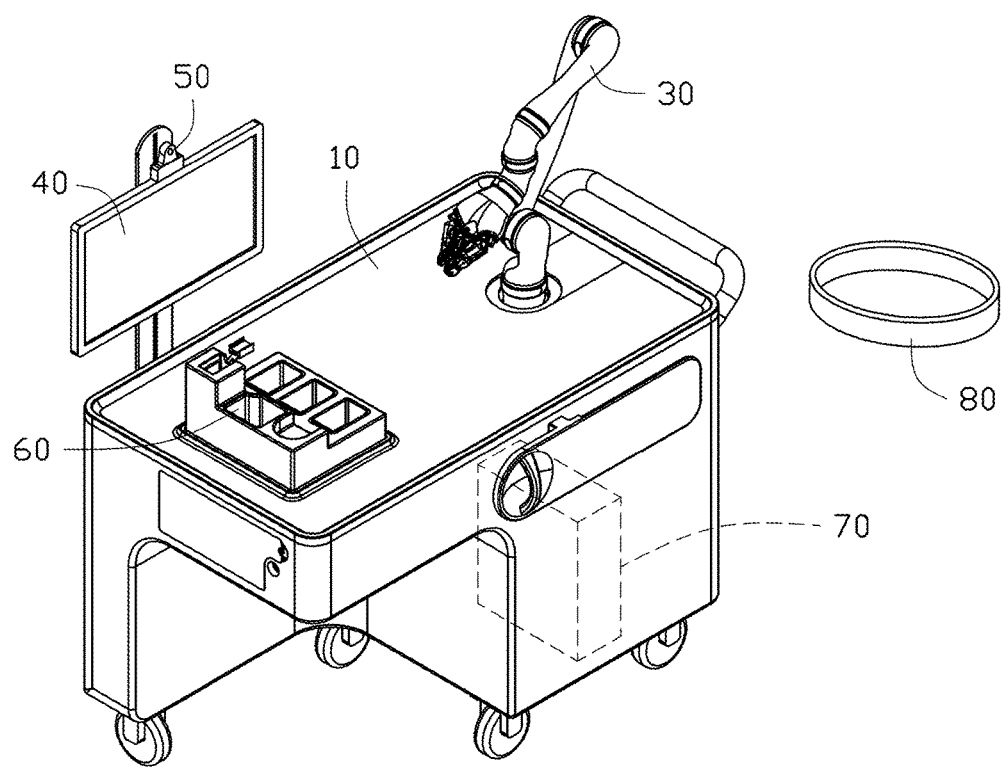
FIG. 1 is a sketch view of a system of controlling robot by brain electrical signal.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The term "comprising" means "including, but not necessarily limited to"; it specifically indicates open-ended inclusion or membership in a so-described combination, group, series, and the like.

FIG. 1 illustrates a system of controlling robot by brain electrical signal which includes a desk 10, a manipulator 30, a screen 40, a camera 50, a dinner plate 60, a host computer 70, and a brain electrical signal detection device 80.

The manipulator 30 is mounted on the desk 10. The screen 40 is mounted on a rear side of the desk 10. The camera 50 is mounted above the screen 40. The camera 50 is used to capture an image of a user. The screen 40 shows icons for the use of the user. The dinner plate 60 is placed on the desk 10. The dinner plate 60 includes a plurality of food receiving areas 61. The plurality of food receiving areas 61 can receive a plurality of different foods. The manipulator 30 fetches foods from the plurality of food receiving areas 61 to the user. The host computer 70 is connected to the manipulator 30, the screen 40, and the camera 50. The brain electrical signal detection device 80 is worn on the head of the user to detect electrical signals generated by the user. The brain electrical signal detection device 80 communicates with the host computer 70 wirelessly, such as by BLUETOOTH, Wi-Fi, infrared light, and so on.

Figure 2:
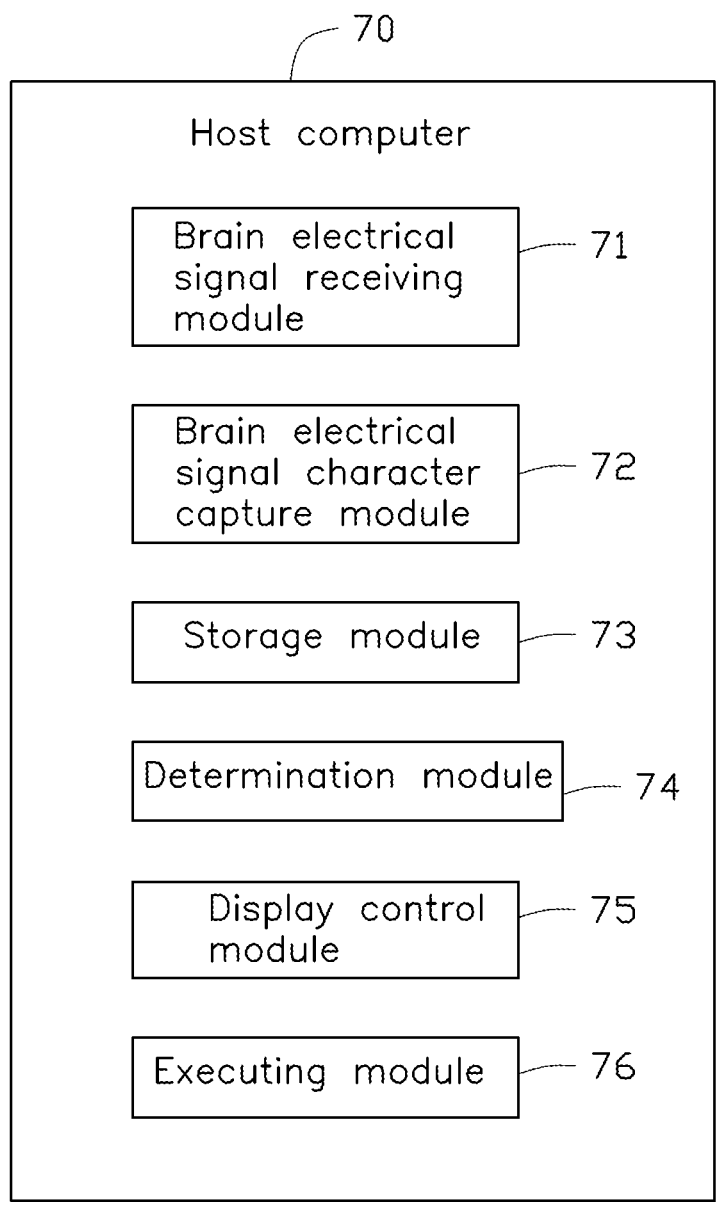
FIG. 2 is a block view of a host computer of the system of claim 1.
Figure 3:
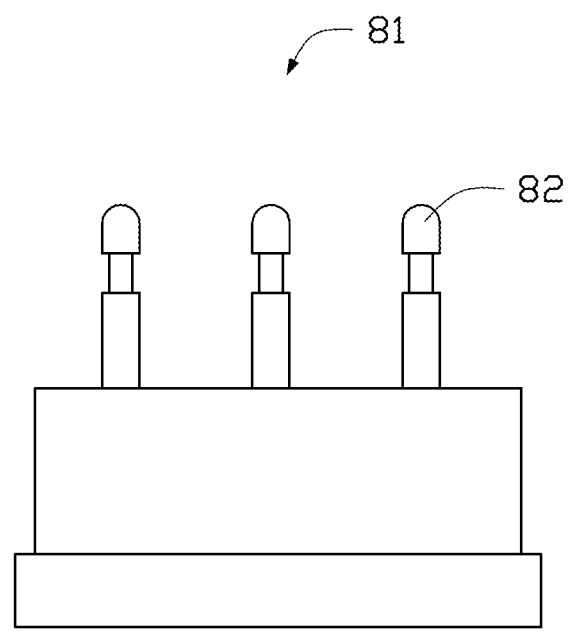
FIG. 3 is a sketch view of a head contact device of the system of FIG. 1.

FIG. 2 illustrates that the host computer 70 includes a brain electrical signal receiving module 71, a brain electrical signal character capture module 72, a storage module 73, a determination module 74, a display control module 75, and an executing module 76. The brain electrical signal receiving module 71 receives the brain electrical signal from the brain electrical signal detection device 80. FIG. 3 illustrates that the brain electrical signal detection device 80 includes a plurality of head contact devices 81. Each head contact device 81 includes a plurality of separate probes 82. The probe 82 can contact scalp through a covering of hair.

Figure 4:
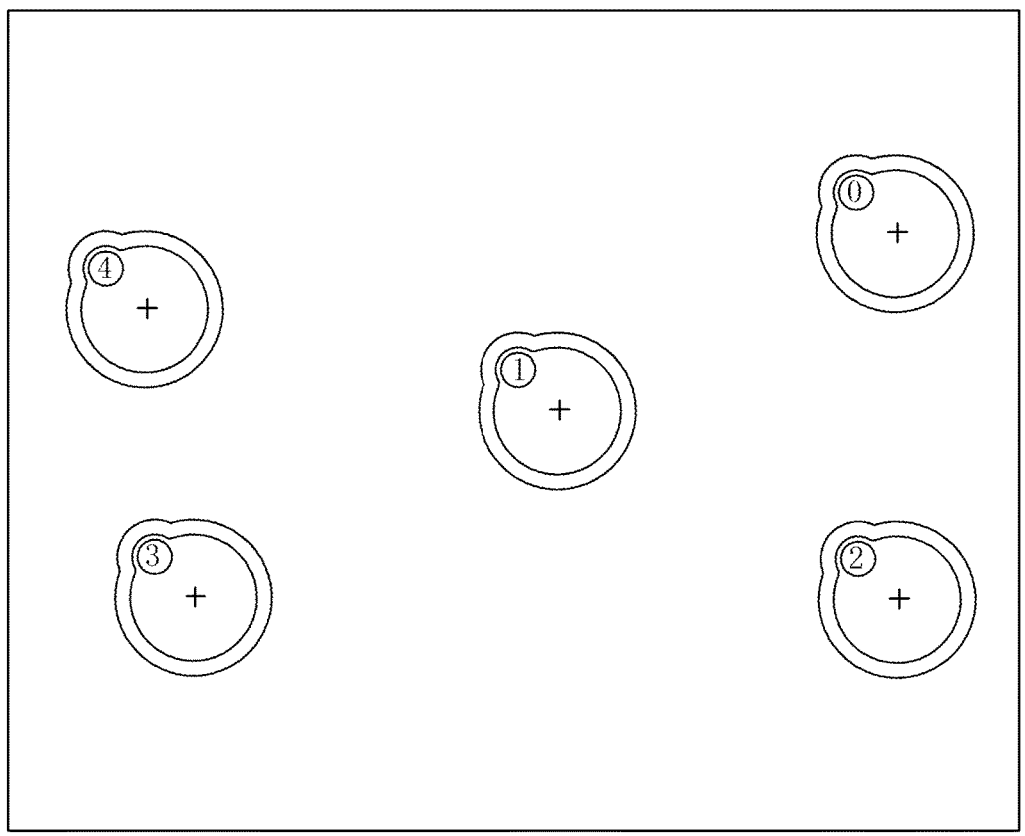
FIG. 4 is a sketch view of a screen showing icons of the system of FIG. 1.

FIG. 4 illustrates the display control module 75 controlling the screen 40 to show a plurality of icons. As shown on FIG. 4, the screen 40 shows five icons: icon 0, icon 1, icon 2, icon 3, and icon 4. The display control module 75 controls the icons to flash at different frequencies. The user generates different brain electrical signals when staring at different icons. For example, when the screen 40 has an illumination frequency of 60 hertz (HZ), the display control module 75 can control the icon 0 to flash at 30 HZ, the icon 1 to flash at 20 HZ, the icon 2 to flash at 15 HZ, the icon 3 at 10 HZ, and the icon 4 to flash at 7.5 HZ. When the screen 40 has a quicker illumination frequency, more icons can be shown on the screen 40 at different frequencies. Further, a frequency of an icon may as well be set to be a quotient of the illumination frequency of the screen 40. For example, when the screen 40 has an illumination frequency of 144 HZ, the icons can respectively be shown as 72 HZ, 48 HZ, 36 HZ, 24 HZ, 18 HZ, 16 HZ, 8 HZ, 4 HZ, and 2 HZ.

The storage module 73 stores a plurality of reference parameters which represent brain electrical signal of normal person.

Figure 5:
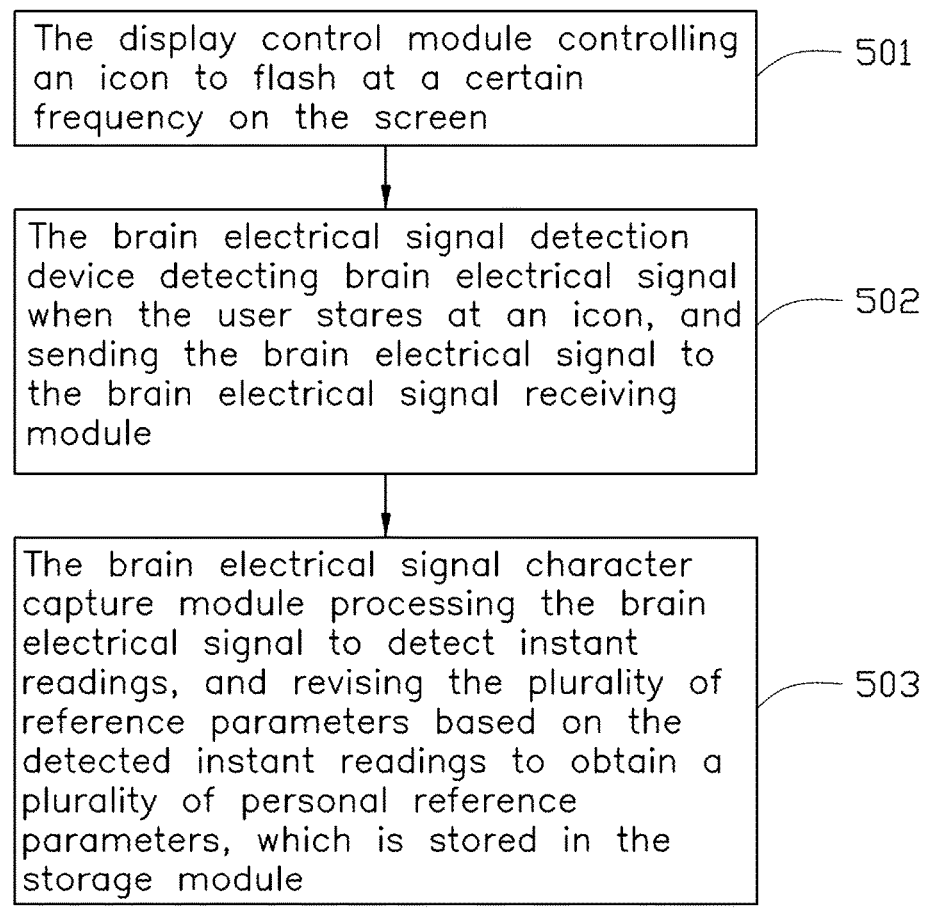
FIG. 5 is a flow chart of the processing of brain electrical signal.

FIG. 5 illustrates a flow chart of one embodiment of processing brain electrical signal comprising following steps:

At block 501, the method comprises the display control module 75 controlling an icon to flash at a certain frequency on the screen 40.

At block 502, the method comprises the brain electrical signal detection device 80 detecting brain electrical signal when the user stares at an icon, and sending the brain electrical signal to the brain electrical signal receiving module 71 of the host computer 70.

At block 503, the method comprises the brain electrical signal character capture module 72 processing the brain electrical signal, for example, filtering the brain electrical signal, transforming the brain electrical signal by a Fourier transform, and calculating energy of the brain electrical signal at some frequency. This process includes detecting instant readings, and revising the plurality of reference parameters based on the detected instant readings to obtain a plurality of personal reference parameters, which is stored in the storage module 76.

The above steps are repeated to obtain personal reference parameters in relation to each icon.

Figure 6:
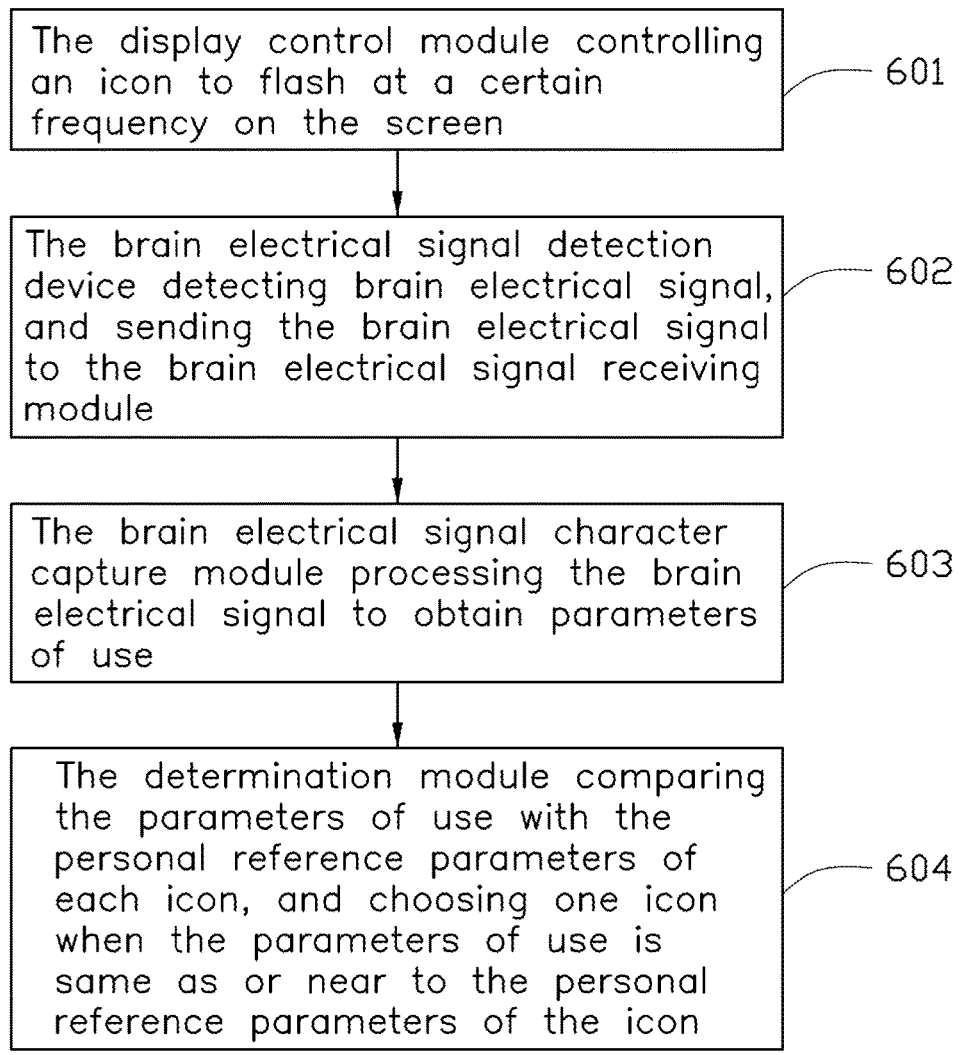
FIG. 6 is a flow chart of the identifying of brain electrical signal.

FIG. 6 illustrates a flow chart of one embodiment of identifying brain electrical signal comprising following steps:

At block 601, the method comprises the display control module 75 controlling an icon to flash at a certain frequency on the screen 40.

At block 602, the method comprises the brain electrical signal detection device 80 detecting brain electrical signal, and sending the brain electrical signal to the brain electrical signal receiving module 71 of the host computer 70.

At block 603, the method comprises the brain electrical signal character capture module 72 processing the brain electrical signal to obtain parameters of use.

At block 604, the method comprises the determination module 74 comparing the obtained instant reading (parameter of use) with the personal reference parameters of each icon, and accordingly choosing one icon when the parameter of use is same as or near to the personal reference parameters of the icon.

Figure 7:
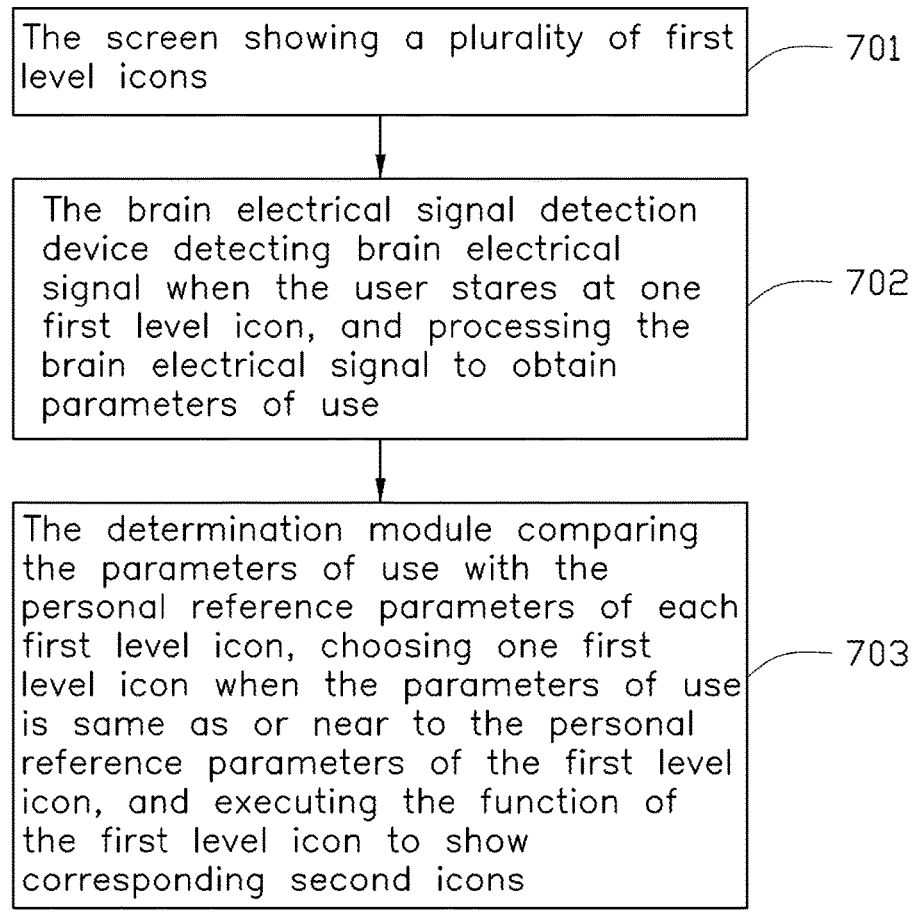
FIG. 7 is a flow chart of a method of controlling a robot by brain electrical signal.
Figure 8:
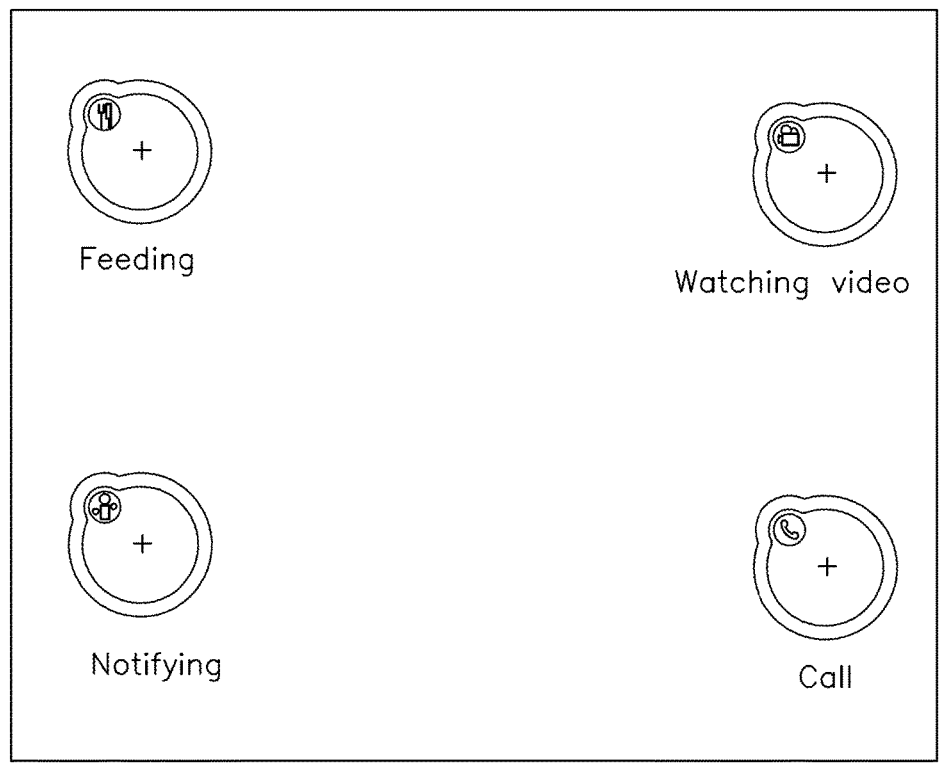
FIG. 8 is a sketch view of the screen of FIG. 4 showing a plurality of item icons.

FIG. 7 illustrates a flow chart of one embodiment of controlling a robot by brain electrical signal comprising following steps:

At block 701, the method comprises the screen 40 showing a plurality of first level icons. FIG. 8 shows four icons, these being feeding, watching video, notifying, and calling.

At block 702, the method comprises the brain electrical signal detection device 80 detecting brain electrical signal when the user stares at one first level icon, and processing the brain electrical signal to obtain parameters of use.

At block 703, the method comprises the determination module 74 compares the parameters of use with the personal reference parameters of each first level icon, one first level icon being chosen when the parameter of use is same as or near to the personal reference parameters of the first level icon, and executing the function of the first level icon. Second, and corresponding, icons are then shown.

Figure 9:
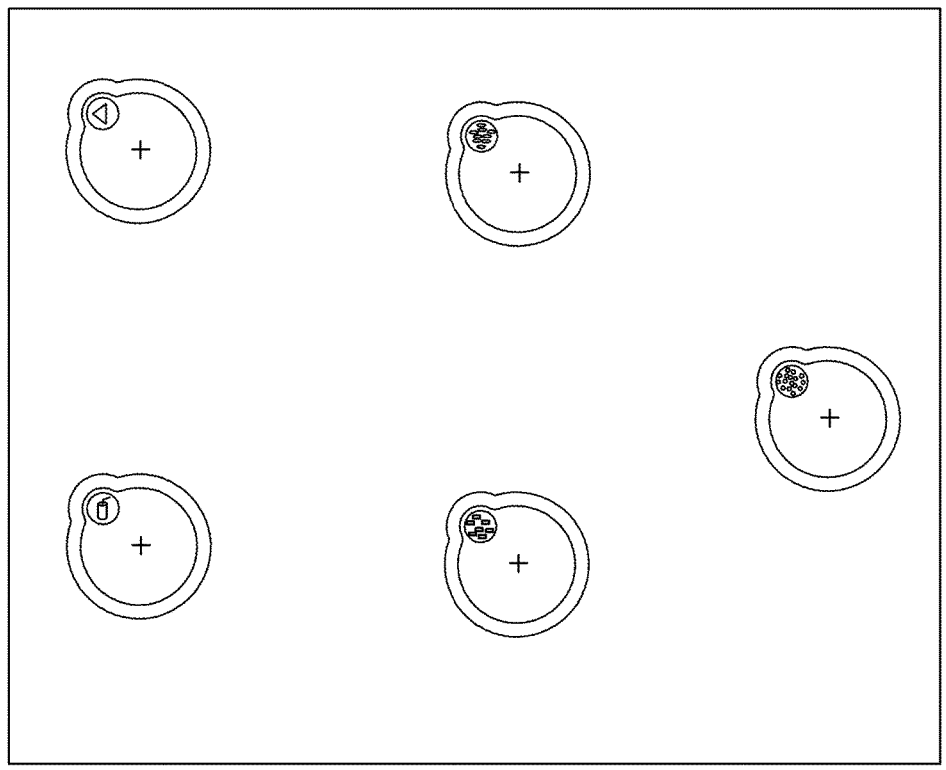
FIG. 9 is sketch view of the screen of FIG. 4 showing a plurality of food icons.

FIG. 9 shows five second icons displayed when the feeding icon of FIG. 8 is chosen. The five second icons are a return icon and four food icons. When the return icon is chosen, the interface of FIG. 8 is again displayed. When one food icon is chosen, the manipulator 30 fetches that food from the dinner plate 60 for the user. The camera 50 captures an image of the user. The host computer 70 determines an elevation of a mouth of the user according to the image, and controls the manipulator 30 to present the food to the mouth.

Figure 10:
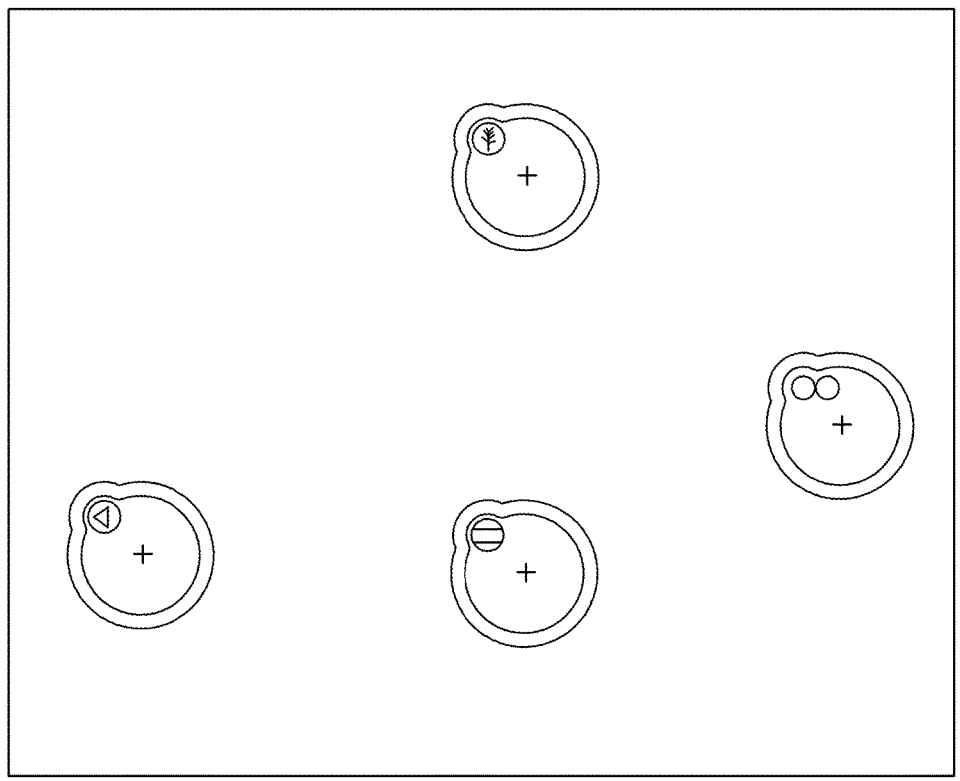
FIG. 10 is a sketch view of the screen of FIG. 4 showing a plurality of video icons.

FIG. 10 shows four second icons when the watching video icon of FIG. 8 is chosen. The four second icons of FIG. 10 are a return icon and three video icons. The three video icons correspond to different video contents.

Figure 11:
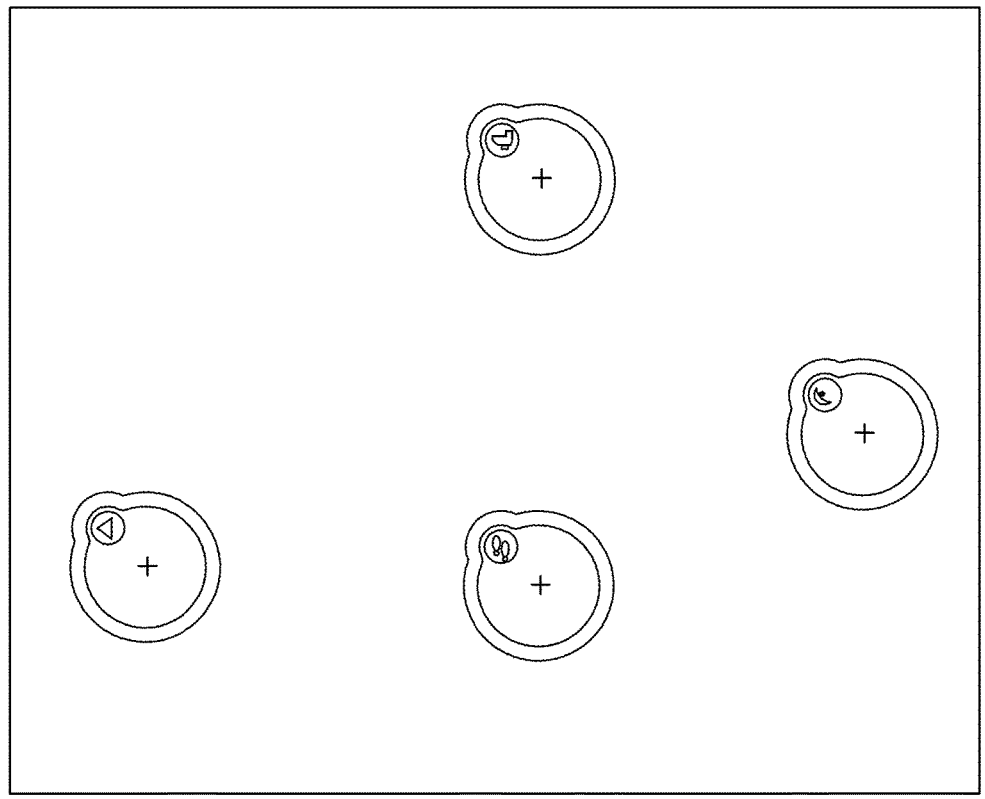
FIG. 11 is a sketch view of the screen of FIG. 4 showing a plurality of notice icons.

FIG. 11 shows four second icons when the notifying icon of FIG. 8 is chosen. The four second icons of FIG. 11 are a return icon and three notice icons. When one notice icon is chosen, the corresponding notice content is broadcasted by the host computer 70. The user's requirement is thereby notified by being broadcasted.

Figure 12:
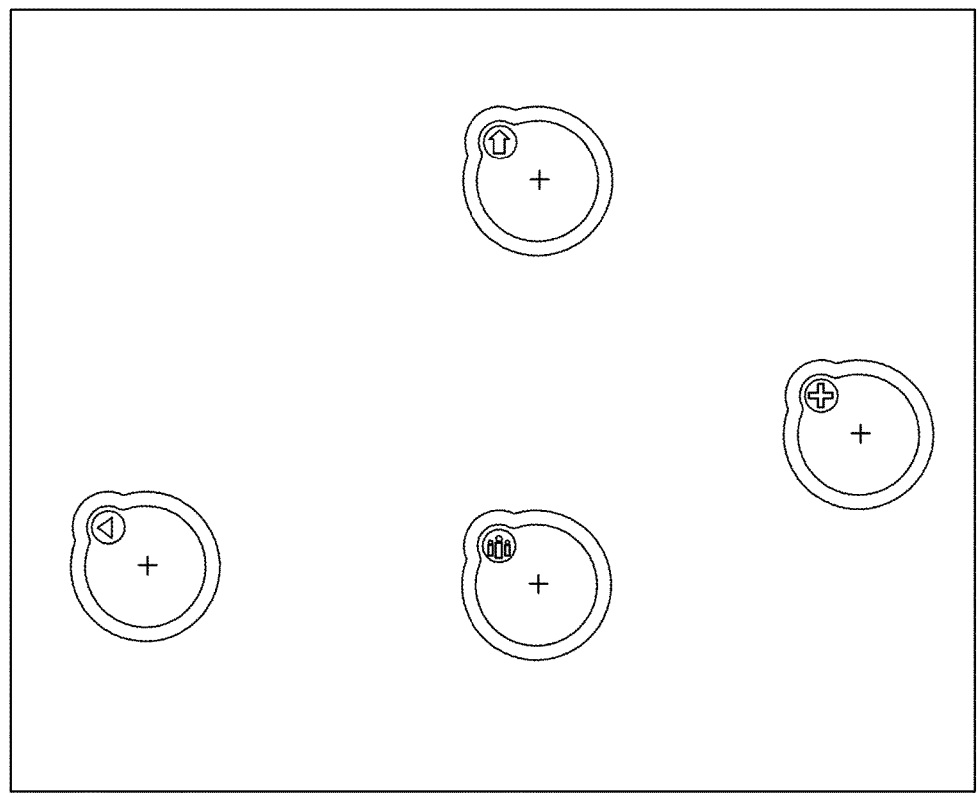
FIG. 12 is a sketch view of the screen of FIG. 4 showing a plurality of phone icons.

FIG. 12 shows four second icons when the calling icon of FIG. 8 is chosen. The four second icons of FIG. 12 are a return icon and three call icons. When one calling icon is chosen, the corresponding person is telephoned.

In the system and method of controlling robot by brain electrical signal, the robot can be simply controlled by brain electrical signal to achieve different functions, such as feeding, watching video, notifying, and calling other people.

The embodiments shown and described above are only examples. Even though numerous characteristics and advantages of the present technology have been set forth in the foregoing description, together with details of the structure and function of the present disclosure, the disclosure is illustrative only, and changes may be made in the details, including in matters of shape, size, and arrangement of the parts within the principles of the present disclosure, up to and including the full extent established by the broad general meaning of the terms used in the claims.

What is claimed is:

1. A system for controlling a robot by brain electrical signal, comprising:
    a screen to show a plurality of icons thereon, and the plurality of icons being configured to flash at different frequencies,
    an electrical signal detection device to detect brain electrical signal of an operator when one of the plurality of icons is stared at by the operator;
    an host computer storing a plurality of personal reference parameters corresponding to the plurality of icons of the screen, the host computer being configured to process the brain electrical signal to get parameters of use, and comparing the parameters of use with the plurality of personal reference parameters to choose the icon which is stared at and to control the robot to execute works represented by the icon.

2. The system as claimed in claim 1, further comprising a desk, a manipulator, and a dinner plate, wherein the manipulator and the dinner plate are mounted on the desk, the dinner plate comprises a plurality of food receiving areas which receive a plurality of different foods therein, the screen shows a plurality of food icons, and the manipulator fetches one food when a corresponding food icon is chosen.

3. The system as claimed in claim 2, further comprising a camera, wherein the camera captures an image of the user, the host computer determines an elevation of a mouth of the user according to the image, and controls the manipulator to present the food to the mouth.

4. The system as claimed in claim 1, wherein the brain electrical signal detection device is communicated with the host computer via wireless manner.

5. The system as claimed in claim 1, wherein the brain electrical signal detection device comprises a plurality of head contact devices, each head contact device comprises a plurality of separate probes, and the probes is configured to contact scalp through a covering of hair.

6. The system as claimed in claim 1, wherein the host computer comprises a brain electrical signal character capture module, and the brain electrical signal character capture module is configured to process the brain electrical signal by filtering the brain electrical signal, transforming the brain electrical signal by a Fourier transform, and calculating energy of the brain electrical signal.

7. The system as claimed in claim 1, wherein the screen shows a plurality of video icons, and each of the plurality of video icons corresponds to different video contents.

8. The system as claimed in claim 1, wherein the screen shows a plurality of notice icons, and the host computer is configured to broadcast a notice content when one notice icon is chosen.

9. The system as claimed in claim 1, wherein the screen shows a plurality of call icons, and each of the plurality of call icons corresponds to one contact person.

10. A method of controlling a robot by brain electrical signal, comprising:
showing a plurality of icons, which correspond to different works, on a screen;
detecting brain electrical signal of an operator by an electrical signal detection device when one of the plurality of icons is stared at by the operator; and
comparing a parameter of the brain electrical signal with a plurality of personal reference parameters corresponding to the plurality of icons of the screen stored in a host computer to choose a the icon which is stared and controlling the robot to execute works represented by the icon.

11. The method as claimed in claim 10, wherein a manipulator and a dinner plate is mounted on a desk, the dinner plate comprises a plurality of food receiving areas which receive a plurality of different foods therein, the screen shows a plurality of food icons, and the manipulator fetches one food when a corresponding food icon is chosen.

12. The method as claimed in claim 11, wherein the camera captures an image of the user, the host computer determines an elevation of a mouth of the user according to the image, and controls the manipulator to present the food to the mouth.

13. The method as claimed in claim 10, wherein the brain electrical signal detection device is communicated with the host computer via wireless manner.

14. The method as claimed in claim 10, wherein the brain electrical signal detection device comprises a plurality of head contact devices, each head contact device comprises a plurality of separate probes, and the probes is configured to contact scalp through a covering of hair.

15. The method as claimed in claim 10, wherein the host computer comprises a brain electrical signal character capture module, and the brain electrical signal character capture module is configured to process the brain electrical signal by filtering the brain electrical signal, transforming the brain electrical signal by a Fourier transform, and calculating energy of the brain electrical signal.

16. The method as claimed in claim 10, wherein the screen shows a plurality of video icons, and each of the plurality of video icons corresponds to different video contents.

17. The method as claimed in claim 10, wherein the screen shows a plurality of notice icons, and the host computer is configured to broadcast a notice content when one notice icon is chosen.

18. The method as claimed in claim 10, wherein the screen shows a plurality of call icons, and each of the plurality of call icons corresponds to one contact person.

* * * * *